(12) United States Patent
Saleh

(10) Patent No.: US 8,858,567 B2
(45) Date of Patent: Oct. 14, 2014

(54) SURGICAL RETRIEVAL DEVICE AND METHOD

(76) Inventor: Rafic Saleh, Aguadilla, PR (US)

( * ) Notice: Subject to any disclaimer, the term of this patent is extended or adjusted under 35 U.S.C. 154(b) by 808 days.

(21) Appl. No.: 11/635,700

(22) Filed: Dec. 6, 2006

(65) Prior Publication Data

US 2008/0091215 A1 Apr. 17, 2008

Related U.S. Application Data

(60) Provisional application No. 60/851,380, filed on Oct. 14, 2006.

(51) Int. Cl.
| | |
|---|---|
| A61B 17/26 | (2006.01) |
| A61B 17/221 | (2006.01) |
| A61B 18/14 | (2006.01) |
| A61B 18/18 | (2006.01) |
| A61B 17/3205 | (2006.01) |
| A61B 19/00 | (2006.01) |

(52) U.S. Cl.
CPC .............. *A61B 17/221* (2013.01); *A61B 18/14* (2013.01); *A61B 2018/1407* (2013.01); *A61B 2018/1861* (2013.01); *A61B 17/32056* (2013.01); *A61B 2017/2212* (2013.01); *A61B 2019/5217* (2013.01)
USPC ......................................................... 606/113

(58) Field of Classification Search
USPC .......................... 606/127, 113, 114, 128, 200
See application file for complete search history.

(56) References Cited

U.S. PATENT DOCUMENTS

| | | | | |
|---|---|---|---|---|
| 3,791,387 | A * | 2/1974 | Itoh | 606/113 |
| 5,846,248 | A | 12/1998 | Chu et al. | |
| 5,997,547 | A * | 12/1999 | Nakao et al. | 606/114 |
| 6,077,274 | A | 6/2000 | Ouchi et al. | |
| 6,183,482 | B1 | 2/2001 | Bates et al. | |
| 6,217,589 | B1 | 4/2001 | McAlister | |
| 6,235,026 | B1 * | 5/2001 | Smith | 606/46 |
| 6,458,145 | B1 | 10/2002 | Ravinscroft et al. | |
| 6,500,182 | B2 | 12/2002 | Foster | |
| 6,656,191 | B2 * | 12/2003 | Ouchi | 606/113 |
| 6,673,080 | B2 * | 1/2004 | Reynolds et al. | 606/127 |
| 6,743,237 | B2 * | 6/2004 | Dhindsa | 606/127 |
| 6,833,000 | B2 | 12/2004 | Levinson | |
| 7,326,220 | B1 * | 2/2008 | Goldstein | 606/113 |
| 2003/0109889 | A1 * | 6/2003 | Mercereau et al. | 606/127 |
| 2004/0059345 | A1 * | 3/2004 | Nakao et al. | 606/113 |
| 2006/0100641 | A1 * | 5/2006 | Teague | 606/113 |
| 2006/0129166 | A1 * | 6/2006 | Lavelle | 606/113 |
| 2007/0016224 | A1 * | 1/2007 | Nakao | 606/113 |
| 2007/0255289 | A1 * | 11/2007 | Nakao | 606/113 |
| 2008/0221587 | A1 * | 9/2008 | Schwartz | 606/113 |

* cited by examiner

*Primary Examiner* — Thomas McEvoy
*Assistant Examiner* — Julie A Szpira
(74) *Attorney, Agent, or Firm* — Donn K. Harms

(57) ABSTRACT

A device for retrieval of organic and inorganic matter during a surgical procedure employing a camera and viewer to ascertain a removal target. The device has a catch basket formed of a plurality of radially oriented shaped wires extending an axis with gaps in-between for camera viewing and light transmission. A mouth aperture area is maximized by formation in a single plane and using wires of a shape to form an oval, crescent, or hexagon. A cauterizing snare may be formed using wires forming the mouth, may project from the catch basket, or may be used separate from the catch basket. Shaped memory material forming the wires maintains the shape of the catch basket, mouth, and snare, despite repeated compressions thereof into catheter housed conduits.

33 Claims, 16 Drawing Sheets

SURGICAL RETRIEVAL DEVICE AND METHOD

This application claims the benefit of U.S. provisional patent application No. 60/851,380, filed Oct. 14, 2006. The disclosed device relates to retrieval devices for use in surgery. More particularly the disclosed device relates to a design and assembly for use in retrieving objects from internal body cavities, either singularly or in combination with a snare or cutting device for removing tissue from the body cavity. The device particularly enhances the capturing and/or retrieving of tissue such as polyps or other pieces of organic or inorganic matter positioned inside the body.

FIELD OF THE INVENTION

Background of the Invention

Laparoscopic or similar surgeries where a tube with a light and a camera lens at the end (laparoscope) is employed to examine organs, check for abnormalities, or perform minimally invasive surgeries are a desirable alternative to prior surgical techniques requiring large incisions. In a similar fashion, procedures in gastroenterology employ such devices to search for and remove colorectal polyps which form on the lining of the intestine.

Such procedures generally employ a small camera adjacent to the instruments inserted through small incisions in the patient's body, or into cavities of the patient's body. Such procedures may involve removal of tissue for a specific ailment, such as the gall bladder, or may be exploratory in nature where tissue samples are taken and removed from the body for examination and testing. Just a few such operations include, but are not limited to, a polypectomy, a bronchoscopy, a bulboscopy, a colonoscopy, a duodenoscopy, an endoscopy and a gastroscopy. Rather than a catheter type device, when used for low invasive procedures through the lower intestine, such devices are also specialized as for endoscopy or in many other specialized versions including but not limited to a gastroscope, or colonoscope, or sigmoidoscope or bronchoscope. These types of devices generally have the video component following a collinear path in a common flexible conduit.

Manually operable surgical devices employed for such procedures inside a patient's body by a surgeon from a position outside the patient are widespread and well known. In a conventional procedure, the cutting and retrieval components employed by the surgeon are located at the distal end of the surgical instrument. In a conventional polyp removal procedure, an endoscope is inserted into an internal cavity of a patient and manipulated to search for any abnormal tissue growths such as polyps. If tissue such as a polyp is located for removal, a wire extending through an elongated pathway in the biopsy channel of the endoscope is translated toward the distal end of the device to project a cauterization loop connected to the wire from the distal end of the pathway running through the endoscope. Using a video display, the surgeon then manipulates the loop and the endoscope from outside of the patient to engage the loop with the polyp. The wire is positioned around the base of the polyp whereafter an electrical current is communicated to the loop to cut and cauterize the region.

As can be ascertained, in such a procedure where tissue is removed for sampling or as an object of the procedure, it is imperative that the surgeon is able to view the tissue in question at the distal end of the surgical device deployed into the patient. Viewing is conventionally achieved over a fiberoptic link from a lens to a video display viewed by the surgeons outside the body of the patient Avoiding interference with the view of the surgeon is particularly important when small tissue samples are being removed, such as a polypectomy, because the polyps being removed are small and easily missed. Further, once removed, they must be located and retrieved with a retrieval component. However, conventional tissue capturing devices for this purpose are formed of nets or netting in a fine mesh. The mesh, especially in the small confines of body cavities such as the intestine, can severely impair the surgeon's view of the tissue by blocking it from camera view. Further, the interconnecting mesh of such devices communicates electrically or offers the potential for such, and therefore such devices are inhibited from functioning as both the snare or tissue removal instrument as well as the catch basket in combination.

As such, using conventional mesh net style retrieval components, subsequent to locating and removing a polyp or other tissue portion by the electrified snare, retrieval and removal of the tissue can be difficult due to view impairment. Additionally, most such net style retrieving components are not easily positionable around the tissue because the netting which is engaged around the mouth of the net impairs or prevents positioning and rotation of the mouth in the small confines of an intestine or other small body cavity.

The device and method herein disclosed and described teaches a tissue capturing component formed of radially oriented wires extending from a mouth portion around a central axis extending forward from the wire engaging it. Unlike most netting or mesh basket collection components, the radially oriented wires forming the catch basket of the device herein disclosed may be fully retracted into the tubing in which they are extended into the body. Further, once translated from the distal end of the tube or conduit carrying it, the formed mouth and radially oriented, disconnected wires forming the catch basket are easily rotated inside even the smallest cavity, since the curved wires are adapted to collapse to yield as small a diameter around the center axis as needed.

Additionally, unlike mesh netting and interconnecting style tissue collection devices which communicate over the entire surface area comprising the basket, the disclosed device herein employs curved and elongated radially oriented wires or ribs providing uninterrupted gaps therebetween. Consequently, a surgeon viewing the intended target using the camera has an uninterrupted view of the tissue to be removed or retrieved through the radial gaps of the disclosed device. Providing the gaps makes for a much improved view for the surgeon on the viewing screen outside the body of the patient. The surgeon can thus easily see even the smallest tissue to be retrieved, and can rotate or manipulate the mouth of the radially formed catch basket over it.

Further, by isolating the wires or ribs forming the basket portion below those forming the mouth, the device herein disclosed can function as a combination snare and cauterizing tissue removal instrument, as well as the catch basket to snatch removed tissue. In a particularly preferred mode of the device, the electrically operated snare removal component may be provided by the mouth of the catch basket. This double duty embodiment of the device is enabled by the same gaps and spacing between the wires or ribs forming the basket and mouth portion since electrical current is not communicated to the other wires from those forming the mouth over the view enhancing gaps.

All embodiments of the device, whether as a combination snare and catch basket, or employed singularly, enjoy additional utility provided by their radially oriented wire formation with radially oriented gaps. Unlike conventional mesh and other interconnected catch basket devices, which once deployed from the tube will not generally translate back into the tube or catheter, a simple translation of the control wire into the conduit carrying it collapses both the mouth portion of the disclosed catch basket and the radial wire portions back into the tube from a first end to the opposite end, thereby collapsing the basket to hold even the smallest piece of tissue, or if not retrieving tissue, then back into the catheter.

Finally, the novel construction of the device herein, with radial components and radial gaps therebetween, allows the device to be employed in a plurality of deployments. The device may be used by itself without a cauterization loop for tissue or material retrieval in its simplest mode. Additionally, it can be employed with a formed cauterization loop on a distal end of the capture basket, or, with the cauterization loop integral to the mouth of the catch basket. Further, the device may be deployed independently of a cauterization loop which would be deployed in parallel positioning of the capture basket and cauterization loop from two conduits in one or two catheters.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for designing other methods and systems for carrying out the several purposes of the present invention of a tissue retrieval system for surgery. It is important, therefore, that the claims be regarded as including such equivalent construction insofar as they do not depart from the spirit and scope of the present invention.

An object of this invention is the provision of a retrieval component for the capturing of tissue or inorganic components from the body.

An additional object of this invention is the provision of such a retrieval component that is formed in a catch basket from radially oriented wires with radial gaps therebetween.

Yet another object of this invention is the provision of such a radially formed component that provides means for improved camera viewing of a target, though the uninterrupted gaps between the radially disposed wires forming it.

Another object of this invention is to provide such a retrieval component that may be used separately or in combination with a cauterization loop at its distal end from a parallel passage.

Yet another object of this invention is to provide such a retrieval component that may be used separately or in combination with a cauterization loop formed around the perimeter of its mouth portion.

An additional object of this invention is to provide such a retrieval component which may be easily rotated inside the body cavity once translated from a collapsed engagement in a deployment tube or conduit.

These together with other objects and advantages which will become subsequently apparent reside in the details of the construction and operation as more fully hereinafter described and claimed, reference being had to the accompanying drawings forming a part thereof, wherein like numerals refer to like parts throughout.

SUMMARY OF THE INVENTION

The tissue capturing component herein described and disclosed features a catch basket which is collapsible for translateable engagement through a conduit into a deployment tube such as a catheter or colonoscope, or similar type device having a control wire or lumen engaged at a first end of the device which runs to a surgeon-manipulable actuator at a second end for controlling the wire at the first end. The capturing component has a catch basket which is translateable from within the distal end of the tube or conduit housing it, and, once so deployed, if not used to capture tissue, may be translated back into the tube from which it was deployed.

This easy translation and forming of the catch basket, along with other utility herein described, is yielded by forming the catch basket from a plurality of radially oriented equidistantly spaced wires extending radially from a mouth portion, around a central axis extending forward from the lumen engaging it.

The device may be employed by itself, or in combination with a snare which may be employed for the cutting of tissue to be retrieved. The snare, if employed in combination with the device, may be engaged to a distal end of a catch basket mouth opposite the manipulation wire or lumen extending through the catheter to the actuators. Or, using the advantages of the gaps between the wires forming the catch basket and the electrical insulation they provide, the cauterization snare may be integral to the catch basket by forming the mouth edge of the catch basket as the cauterization snare. Or, a double lumen embodiment of the device might also be employed where the cauterization snare and the capturing component or catch basket translate from the distal end of a catheter or endoscope or other such component and are controllable independently.

The device, once extended from the distal end of the tube or conduit carrying it, employs a formed mouth portion having two mirrored side edges extending in the same plane to yield a maximum sized opening for the basket. As noted above, this mouth portion may double as the cauterization snare in a particularly preferred mode of the disclosed device. From the mouth portion of the catch basket, extending around the axis defined by the wire or lumen engaged to the device, are a plurality of equidistant, radially oriented, disconnected catch members, which combine to form a catch net. Gaps are defined in between each pair of catch members forming the catch basket.

Because of the radial orientation of both the members forming the catch basket and the two side members forming the planar mouth at substantially 180 degrees, a maximum diameter opening is achieved to encircle the tissue to be retrieved, thereby allowing for capture and retrieval of both large and small targets.

Further, in one embodiment of the device, the formed basket is adapted for rotation when positioned in the body by rotation of control wire adapted to communicate rotation from the handle to the basket. The elongated angled nature of the members forming both the basket and the mouth, allow easy rotation of the entire structure in even the smallest diameter cavity. This is because the curved and elongated radially disposed wires, forming the ribs and mouth portions of the catch basket, are shaped using memory materials to shapes that elongate and flex to accommodate rotation in the dimensions of its surroundings.

Enhanced camera viewing from views provided by conventional mesh baskets is provided by the elongated substantially equal sized, radial gaps defined by the voids formed between the elongated wire members. Once deployed, the device may be easily positioned with using the enhanced viewing and rotating capabilities, provided by its radial construction. If not used for a tissue capture, great utility is provided by the ability to fully recapture the device back into the deployment conduit. This recapture is initiated by a reverse translation of the lumen or control wire attached to the deployed catch basket to pull it back into the catheter carrying the device. The unique radial formation of the mouth and ribs of the device, and voids rather than confections in between, will allow for re-collapse of both the mouth portions, and the radial wire portions, and consequently easy translation back into the catheter. If employed to capture tissue or anything else, translation of the device back into the catheter also causes the mouth portion to close and create an ever shrinking closed capture basket. The device will thus shrink in size to hold and retrieve even the smallest piece of tissue.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing description and following detailed description are considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

DETAILED DESCRIPTION OF THE INVENTION

Figure 1:
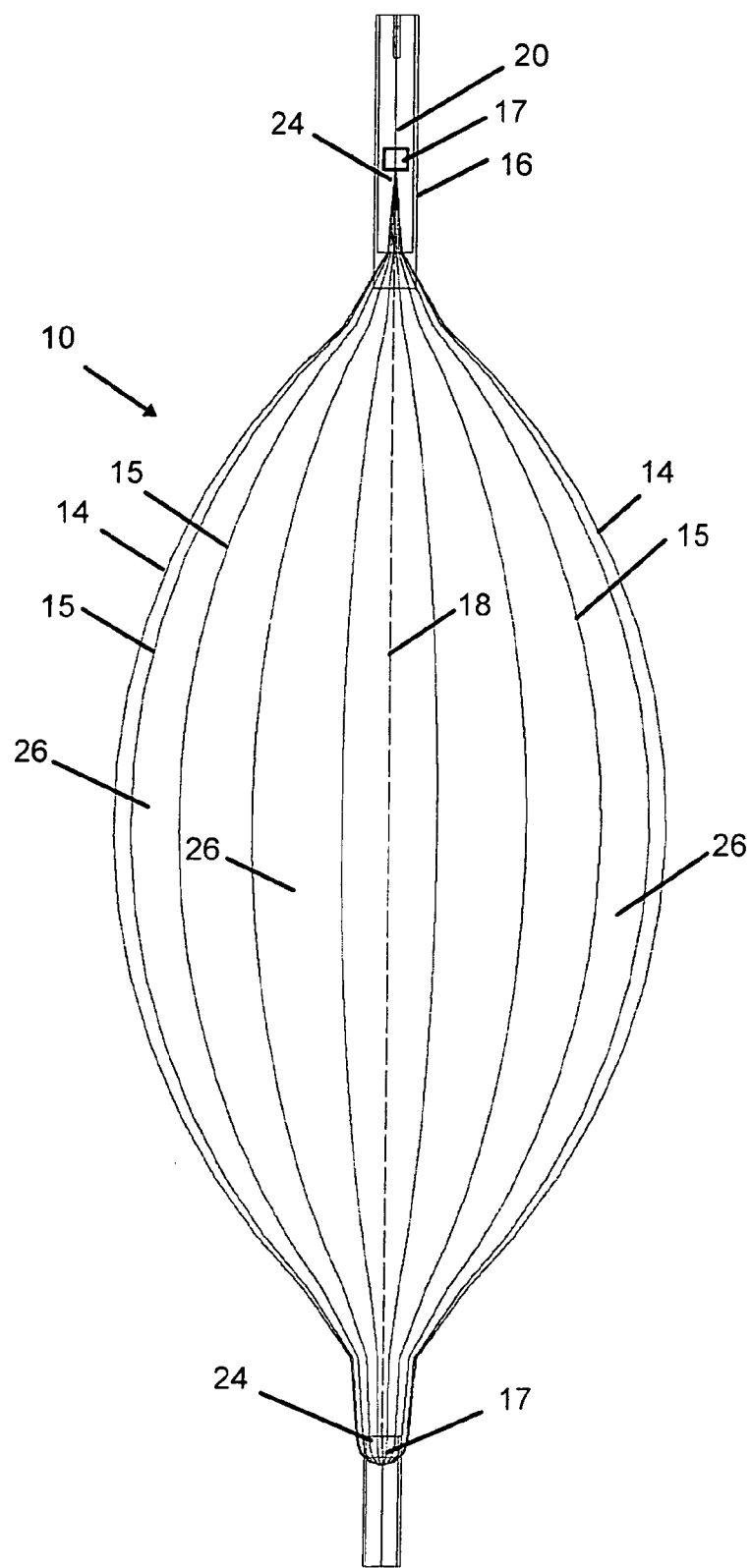
FIG. 1 shows a top plan view of the device showing the mouth formed at the widest point of the radially deployed wires forming the catch basket.
Figure 2:
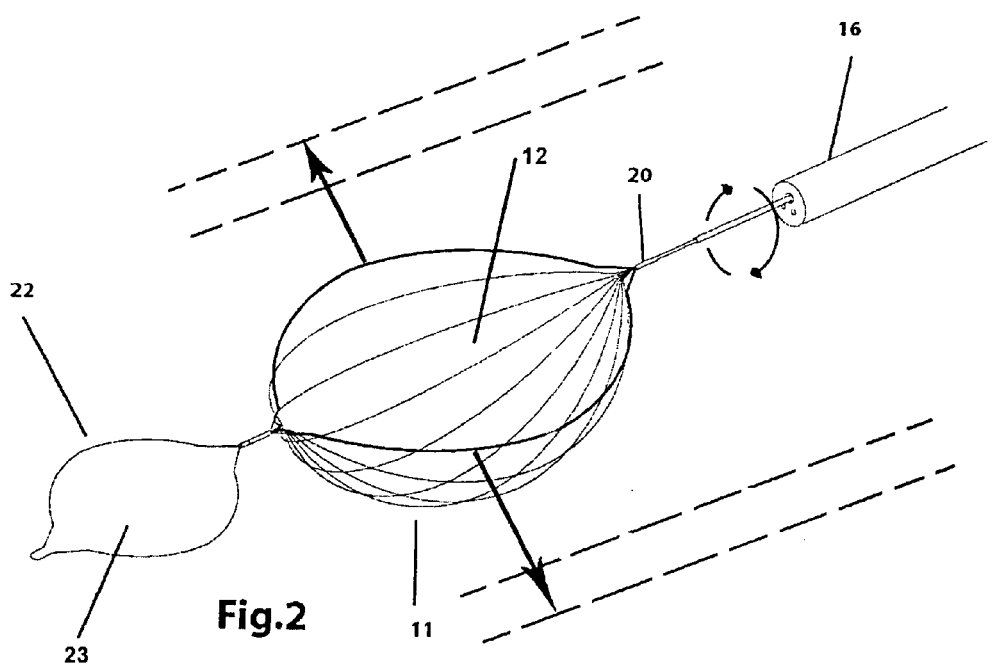
FIG. 2 depicts the device deployed from the distal end of a single lumen catheter with a snare engaged to the distal end of the device.
Figure 3:
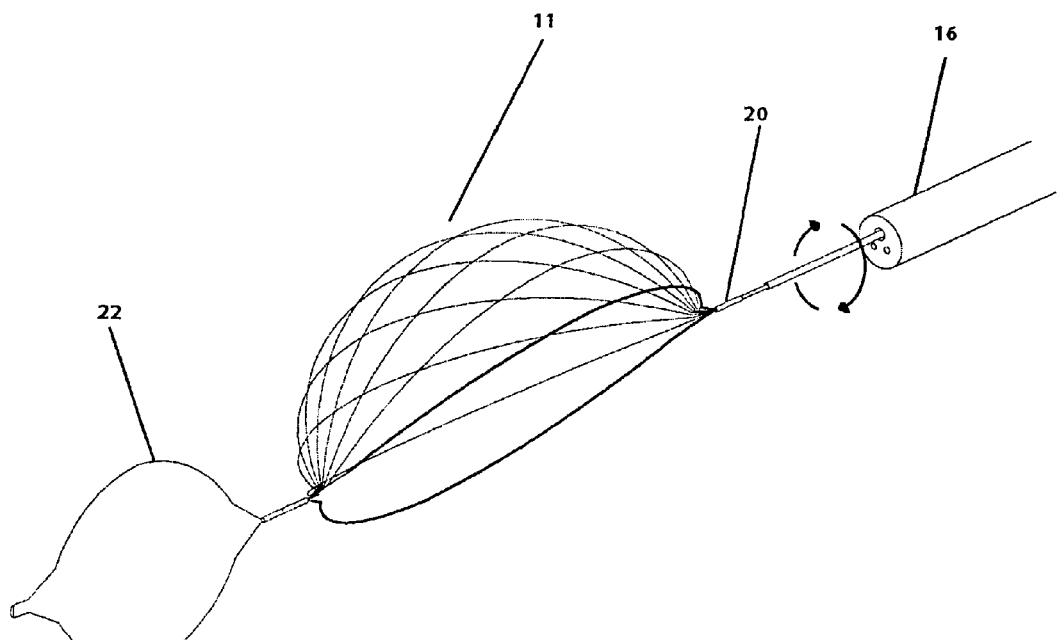
FIG. 3 depicts the rotation capability of the device once deployed from the catheter.
Figure 4:
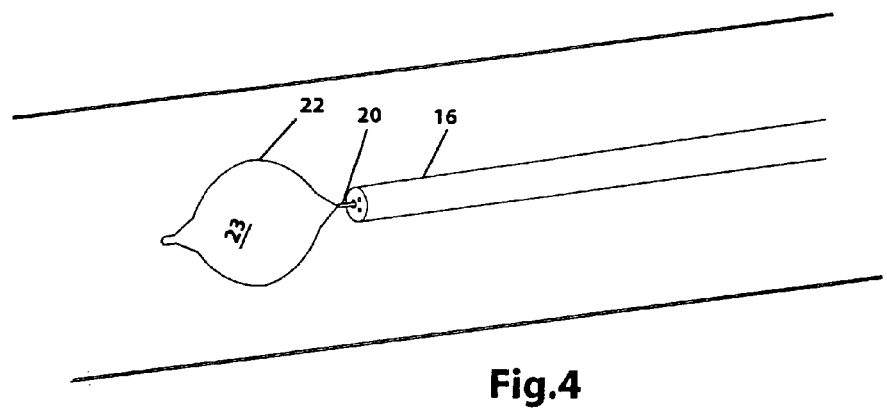
FIG. 4 shows the snare engaged to the distal end of the device, as it is first translated from the distal end of a catheter or endoscope or similar type device such as a gastroscope, colonoscope, sigmoidoscope or bronchoscope.

Referring now to the drawings in FIGS. 1-24, wherein similar parts are identified by like reference numerals, there is seen in FIG. 1 a top plan view of the device 10 showing a mouth or aperture 12 defined by two radially oriented first wires 14. Also shown are radially oriented secondary wires 15 formed spaced from each other and the first wires 14. The first and secondary wires are held in registered engagement substantially equidistant in their radial orientation by a swag 17 or canola or other means for fixed engagement, for holding all of the respective wires in their respective spaced radial positions to form the catch basket 11 with a planar mouth. Because the first wires 14 and second wires 15 are formed from a shape-memory material such as polymers or metal alloys such as nickle-titanium which are light, flexible, strong, they will repeatedly reassume a formed shape which it memorized to the material using heat or other processes. Formed of such material, the wires 14 and 15 are especially well adapted to straighten when pulled into the catheter 16 and reassume their memorized shape once translated from the catheter 16. Further, the formed catch basket 11, because of the radial orientation and spacing and ability to re-compact once deployed, may be retracted back into the catheter 16 if deployed and not used for a tissue capture. This provides an especially useful device since it is much easier to retrieve from body cavities if recaptured into the catheter 16. The same radial orientation of the catch basket 11 yields equal utility when the device 10 is employed in combination with an endoscope or other devices of such design such as a gastroscope, colonoscope, sigmoidoscope or bronchoscope depicted in FIGS. 4-6, all of which employ translateable components along with an optical video component which follow collinear or parallel pathways through the interior of an inserted flexible tube or conduit. Consequently, while the specification describes the device 10 and its components relative to deployment from an elongated conduit in a catheter 16, it may be employed with equal or greater utility with any type of surgical or examination device which is used for surgeries or exploratory procedures in a human or animal.

Both first wires 14 are shaped substantially the same and are positioned opposite the center axis 18 in the same plane or 180 degrees apart to form mirror images of each other. This is an especially preferred mode of formation in all modes of the device 10 and in all shapes, as testing has shown an enhanced ability of such a planar mouth to capture a larger range of tissue in use. The result of maintaining the shaped first wires 14 defining the mouth or aperture 12 fixed in the same plane, yields the largest possible aperture or mouth 12 through which tissue or items being captured may traverse. The resulting device 10 formed by the shaped first wires 14 and similarly shaped second wires 15 which are radially oriented around the axis 18, and substantially equidistant from any adjacent first 14 or second wire 15, is a catch basket 11 in the shape defined by the shape of the wires.

A first end of the catch basket 11 of the device 10 is engaged to the distal end of a control wire or lumen 20 tranlateably engaged within a conduit running through the catheter 16. In one of the single lumen modes of the device 10, shown and described herein, at the second end or distal end of the device 10 opposite the connection to the lumen 20, is engaged a snare 22. The snare 22 is shown in one favored mode of the device 10 with its center aperture 23 in substantially the same plane as the mouth 12 defined by the first wires 14. Of course those skilled in the art will realize other angular relations can be employed and such are anticipated. Also, the unique radial orientation of the first and second wires forming the catch baskets 11 of the device 10 and the gaps 26 therebetween provide for numerous configurations in combination with, or without, the cauterizing snare 22. As noted below, the snare 22 in particularly preferred modes of the device 10 in differing shapes can be provided by the first wires 14 defining the aperture 12. This especially preferred mode would thereby allow for positioning the formed catch basket 11 around the tissue 30 being detached.

Means to maintain the first wires 12 and second wires 14 radially oriented around the axis 18 and substantially equidistant from adjacent first or second wires, and to maintain the first wires 14 mirrored in the same plane, are provided at engagement points 24 provided by and depicted as the swag 17. However, other such means as would occur to those skilled in the art are anticipated. If the device 10 employs a snare 22 integral with the first wires 14 forming the aperture 12, the secondary wires 15 would be electrically insulated at the engagement points 24 from the two first wires 14, which would be uninsulated and therefor adapted for electrical reaction with the body of the patent when energized.

The catch basket 11 in all shapes and configurations of the device is as can be see, formed of a plurality of similarly shaped first wires 12 and secondary wires 14 disposed in a half circle around the axis 18 defined by the lumen 20. All the first and secondary wires are also substantially equidistant from each other. Formation of this configuration to the desired shape of the catch basket 11 and planar aperture 12 is accomplished on a jig or other forming component during manufacture using memory material which maintains the desired shape afterwards. Engaging the first and secondary wires at engagement points 24 using means for registered engagement such as a swag or canola 17 thereafter holds them in their respective desired spacing from each other, thereby yielding the desired gaps 26 therebetween on deployment. Once the proper shape and spacing are achieved, and the wires are placed in a fixed and registered engagement relative to each other, the device 11 is ready for use by engagement to a lumen 20 or other translatable wire, and collapses into the conduit at the distal end of a catheter 16.

The radial orientation and substantially equidistant spacing in all embodiments of the device 10 creates a plurality of substantially equal gaps 26 defined by the areas between the first and second wires and any adjacent second wire. The dimension of the gaps 26 is determined by the number of second wires 15 equally spaced around the axis 18 between the two in-plane first wires 14. The more second wires 15 included in the device 10, the smaller the gaps 26, and conversely the less included, the larger the gaps 26. These material-free gaps in a fixed radial orientation, combined with the thin wires 15 also in a radial orientation, provide an especially well-preserved field of view for any camera which is inserted to provide a view of the cavity. Since capture of tissue such as a polyp 30 requires that the user watch a video depiction of the camera view, when the camera is operatively deployed adjacent to the distal end of the catheter 16, an excellent and relatively unobstructed field of view is provided to the user to guide the catch basket 11 to ensnarl and retrieve any target, since the first and second wires in the radial orientation do not loom large in the field of view provided through the unobstructed gaps.

As shown in figures depicting the various modes and shapes of the device 10, once it is deployed from the catheter 16, it is translateable toward and away from the catheter 16. In a first preferred mode of the device 10, the catch basket 11 is engaged to a stranded control wire 20 and is rotatable in the body cavity by rotating the catheter 16. This rotation is possible in all the shapes of the device 10 shown in the drawings and with the snare 22 integral to the aperture 12 defined by the first wires 14 such as in FIGS. 12, 14, and 19, or with the snare 22 engaged at the distal end of the catch basket 11 such as in FIGS. 2, 10, 16, and 19, or in deployments where the snare 22 is separately positioned from the catch basket 11 such as in FIGS. 11, 17, and 24.

In an especially preferred alternative embodiment of the device, the catch basket 11 may be rotated 360 degrees around the axis 18 by rotation of a specially constructed solid or unitary control wire 20 adapted to rotate within the catheter 16 through manipulation of a handle engaged for rotation. This rotation ability is particularly useful in capturing tissue or inorganic matter in the device 10 through the mouth 12 defined by the two first wires 12. Employment of the solid control wire 20 enhanced that rotation ability by providing two means for rotation of the catch basket 11.

As noted, while being manipulated over a target object or tissue piece such as a polyp 30, user viewing of camera produced real-time video is particularly enhanced by the gaps 26 between the first and second wires, and their radial orientation around the axis 18. The gaps 26, having no connections or communication between adjacent wires forming them, provide not only an unhindered view for a camera, they also provide an unhindered pathway for the projected light from the camera assembly which accompanies the camera into a dark body cavity. This allows more light to transmit through the gaps and to hit and reflect from a target back to the camera, thereby yielding an enhanced video depiction. Unlike mesh type capture nets, which lack gaps 26 because they are woven or knitted with material and thereby impede both light transmission and video capture by the camera, the disclosed device 10 provides excellent viewing and yields enhanced depth of field focusing due to the availability of unobstructed pathways for viewing and light transmission.

In uses as depicted in FIG. 4-9, the device 10 is positioned in the body in a collapsed position inside the catheter 16. The snare 22, if engaged on the distal end of the catch basket 11, while pictured as deployed from the distal end of the catheter 16, may also be collapsed into conduit communicating with the distal end of the catheter 16 during deployment and routing to a position in the body of the patient. Of course if the snare 22 is integral to and formed by the first wires 14 defining the aperture 12, such as in FIG. 12, it and the rest of the formed catch basket 11 would be collapsed into the conduit of the catheter 16.

Figure 5:
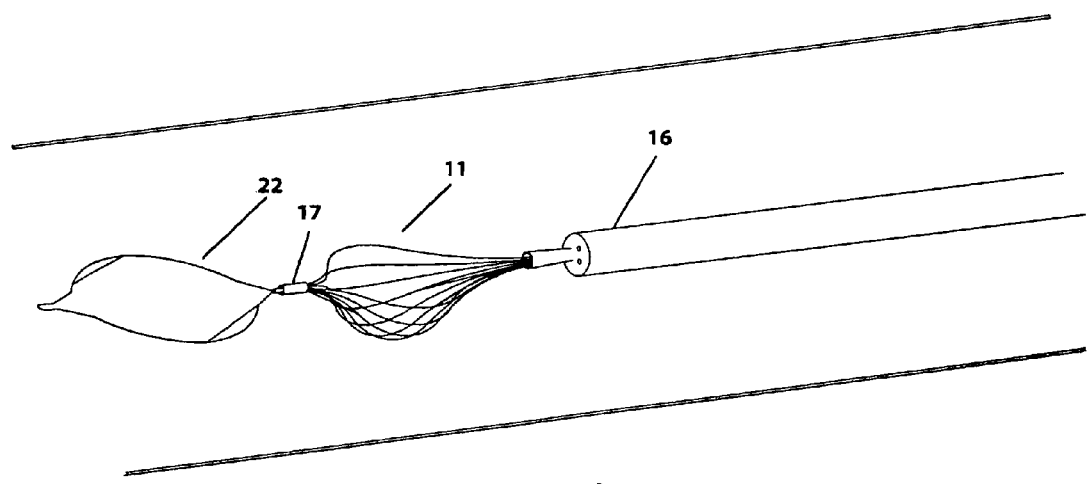
FIG. 5 depicts a perspective view of the device of FIG. 4 with both the snare and the catch basket device deployed from the distal end of single lumen catheter.
Figure 6:
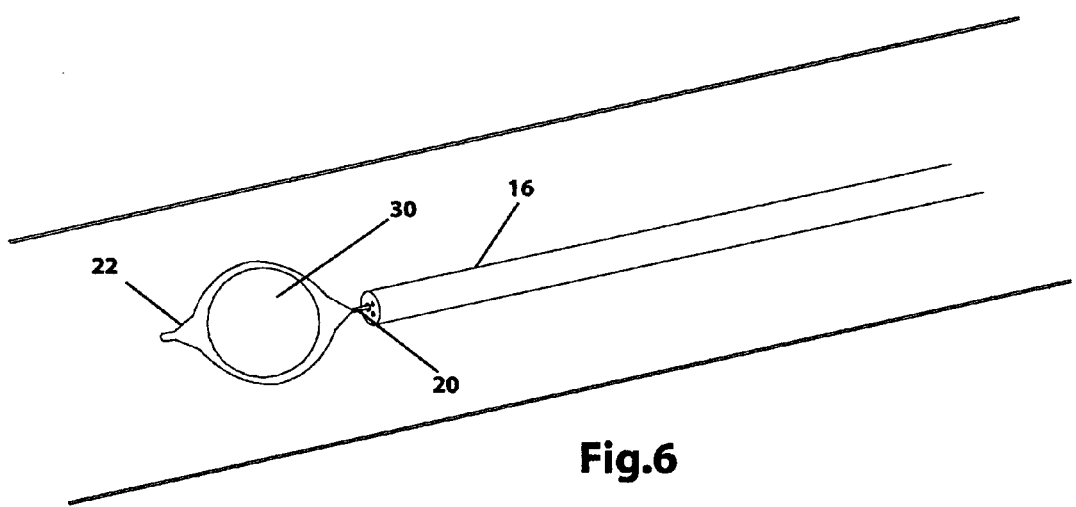
FIG. 6 depicts the snare deployed from the catheter type device and being employed to slice tissue.
Figure 7:
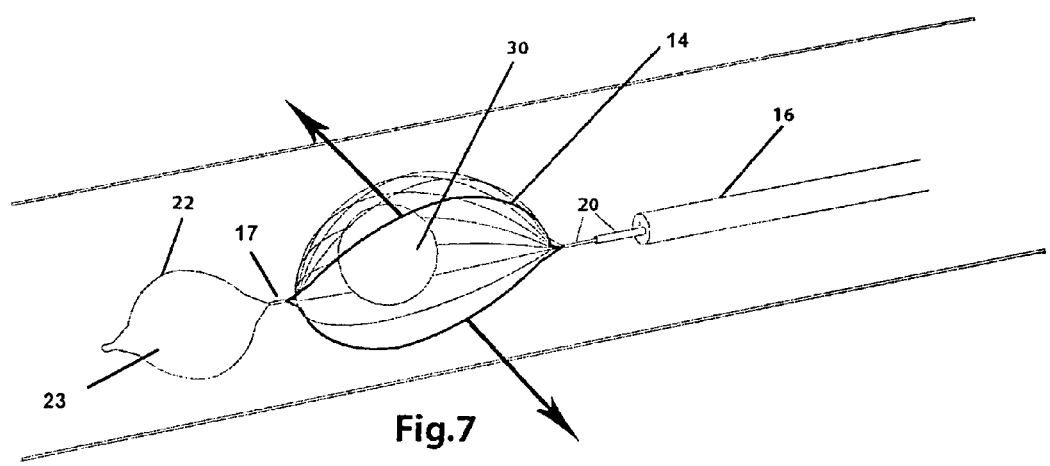
FIG. 7 depicts the device of FIG. 6 wherein the catch basket has been translated from the catheter and is being rotated to allow the mouth to encircle the tissue removed by the snare.
Figure 8:
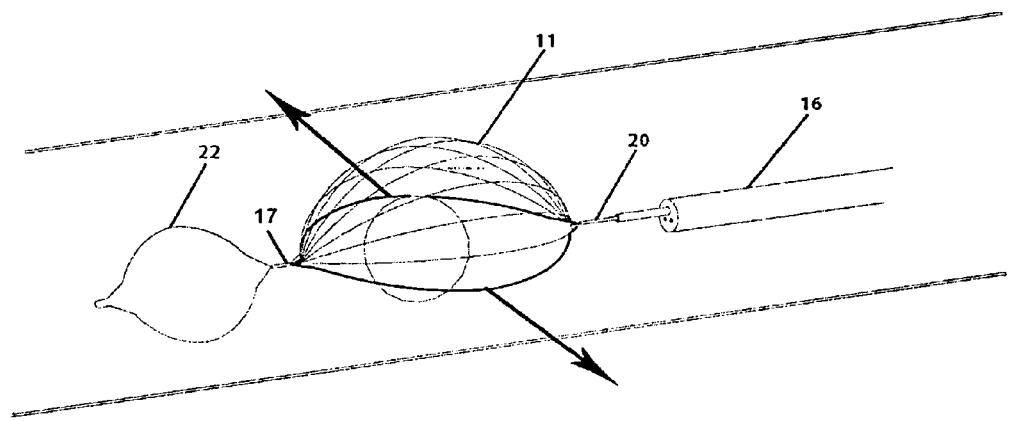
FIG. 8 depicts the catch basket rotated around the tissue which is supported on a surface.
Figure 9:
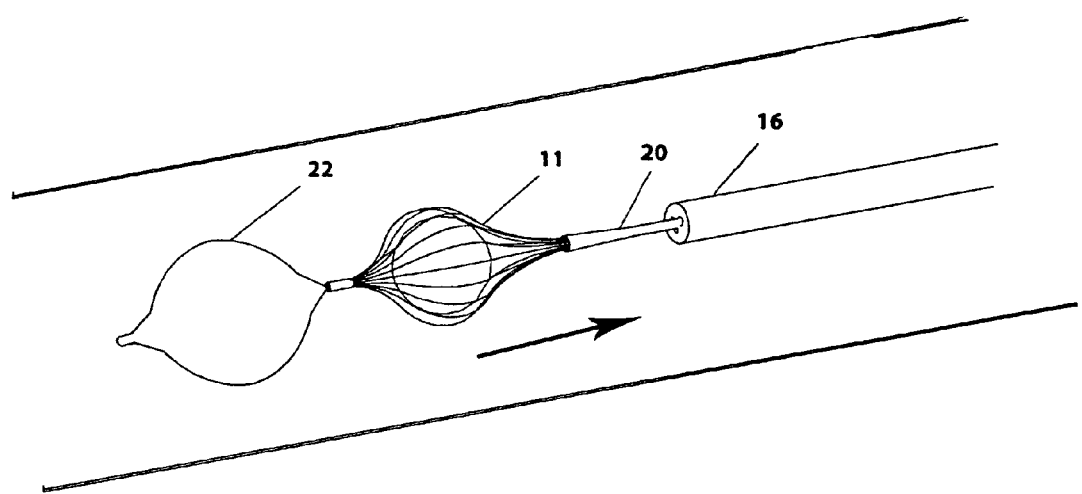
FIG. 9 depicts the translation of the lumen back into the catheter and the resulting encirclement of the tissue placed into the catch basket.
Figure 10:
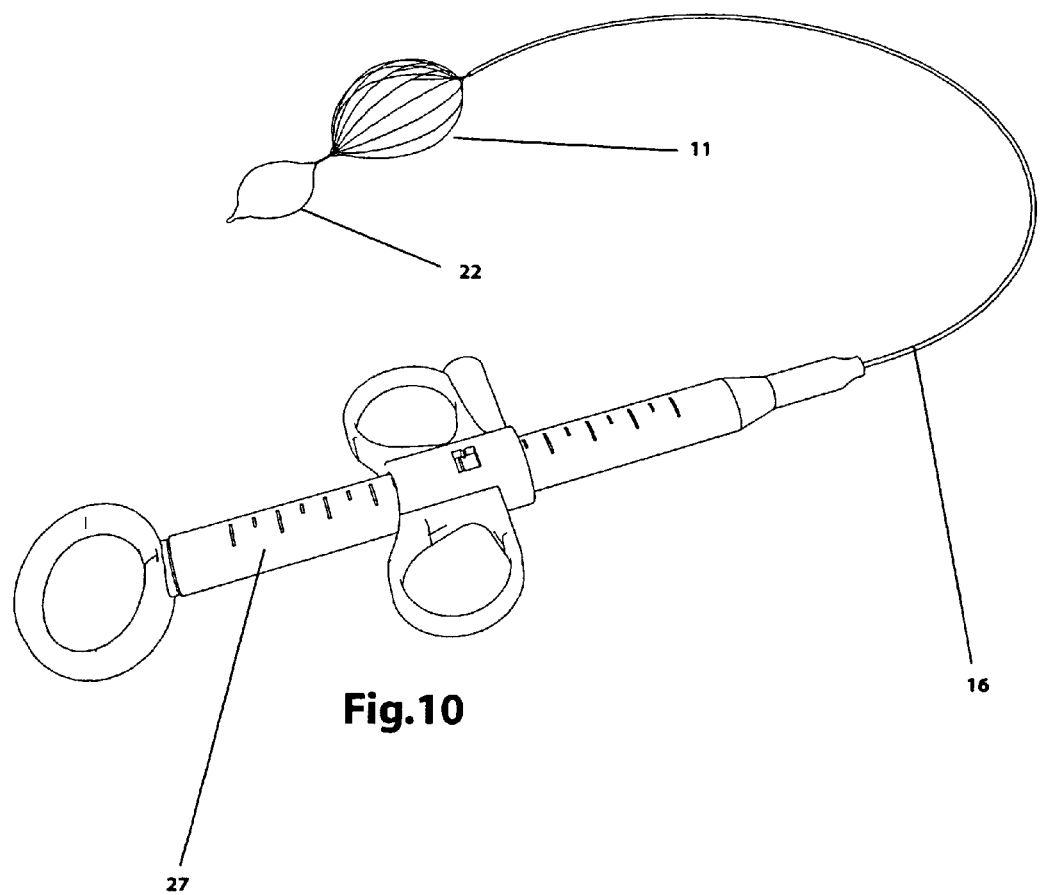
FIG. 10 shows the device with the catch basket engaged to the distal end of a single lumen catheter and the snare engaged to the distal end of the catch basket.

Upon viewing tissue 30 to be removed from the patient, the snare 22, whether integral to the aperture 12 of the catch basket 11 or projecting from the leading end of the catch basket 11, is positioned to encircle the tissue 30 by translating the lumen 20 or the catheter 16 or both in the body. As depicted in FIG. 5, the snare 22 is then energized with an electric current to concurrently cut and cauterize the tissue 30 being removed.

In the embodiments of the device 10 where the catch basket 11 is separate from the snare 22, or has the snare 22 positioned on the leading edge of the catch basket 11, once the tissue 30 or other target of capture is loose from engagement to the body of the patient, the catch basket 11 is positioned to remove the target. As noted, two features of the device herein disclosed provide great utility in that quest. First, as noted earlier and shown in FIGS. 2-3, the device 10 is fully rotatable once deployed from the confines of the catheter 16 by rotation of the lumen 20. Second, the gaps 26 and radial orientation of the wires provide unhindered viewing of the tissue 30 or other target for the catch basket 11 while the surgeon is translating the lumen 20, the catheter 16, or rotating the lumen 20 as a means to rotate the mouth 12 of the catch 11 basket to encircle the tissue 30 or target. With this unhindered view through the gaps 26 and the ability to translate and rotate the mouth 12, capture of tissue 30 or other target objects is greatly enhanced and time reduced for the exercise. As noted earlier, the elongated curve of the first and second wires forming the catch basket 11 makes them particularly pliable to a reduction of the diameter of the body cavity in which they are placed. Essentially the memory material forming the wires 14 and 15 biases the wires to form the largest diameter possible in the body cavity they are placed. However, the elongated curve of the wires also adapts them to straighten and accommodate a passage or cavity narrower than the diameter of the mouth 12 which is the maximum diameter of the formed catch basket 11.

In all embodiments of the device 10 with the snare 22 integral to the aperture or separate, once the tissue 30 or other target for the catch basket 11 is engaged within the cavity defined by the area between the planar of the mouth 12 and the radially oriented second wires 15, the surgeon translates the lumen 20 back toward the catheter 16. This translation has a pulling effect upon the catch basket 11 and much like a Chinese puzzle, the elongated curved or shaped wires forming the basket will tend to both collapse and engage upon the tissue 30 and the first wires 14 forming the mouth will tend to wrap around the exterior of the tissue 30 or target. Pulling a portion of the first and second wires into the catheter 16 by translation of the lumen 20, will shrink the formed cavity further by collapsing the side of the cavity that is proximal to the lumen 20 to thereby tighten the grip of the catch basket 11 upon the target. So captured, the tissue 30 or targeted matter may be removed from the body by removal of the distal end of the catheter 16 from the body.

Figure 11:
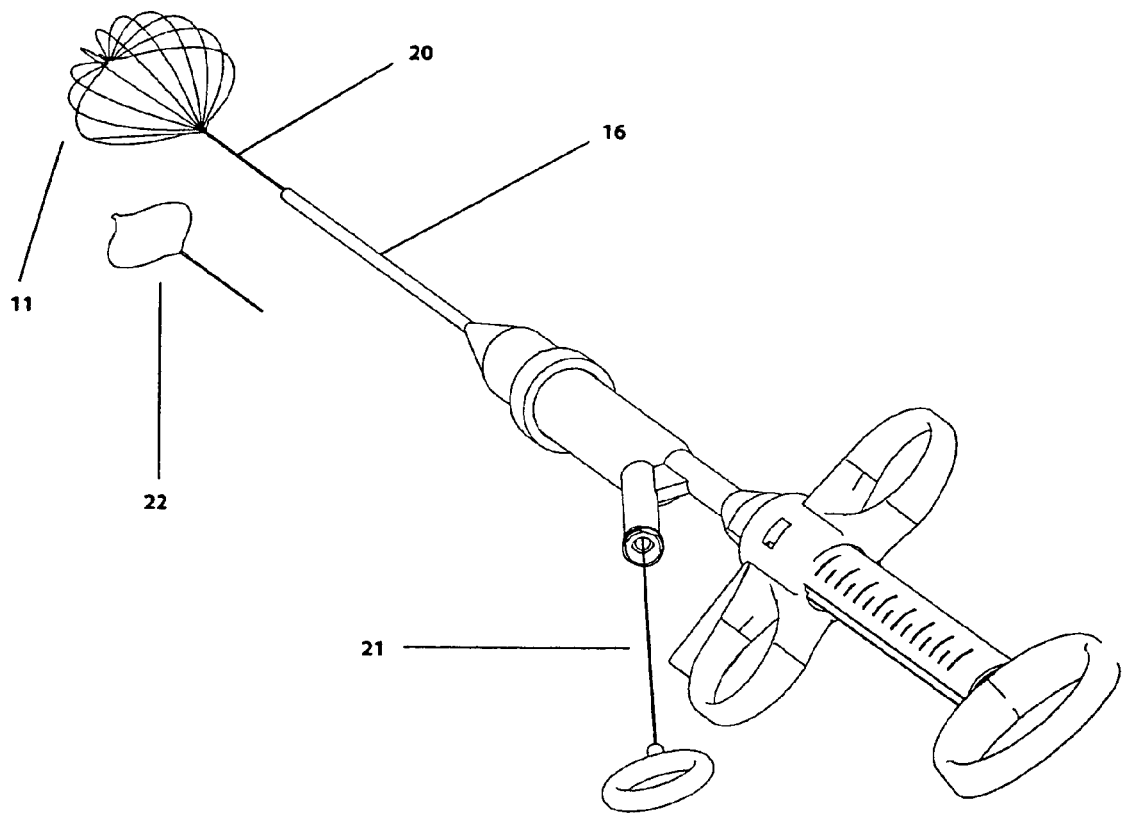
FIG. 11 depicts a double lumen embodiment of the device where translation and control of both the snare and the catch basket are provided by independent translating control wires or lumens in the catheter.
Figure 12:
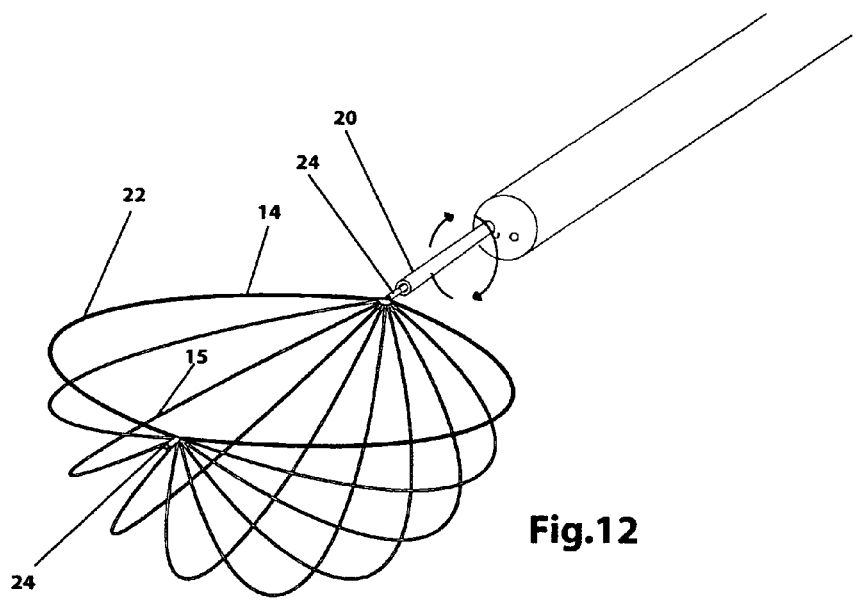
FIG. 12 shows an especially preferred embodiment of the device wherein the cauterization snare is integral to the mouth of the catch basket which has an overall oval shape.
Figure 13:
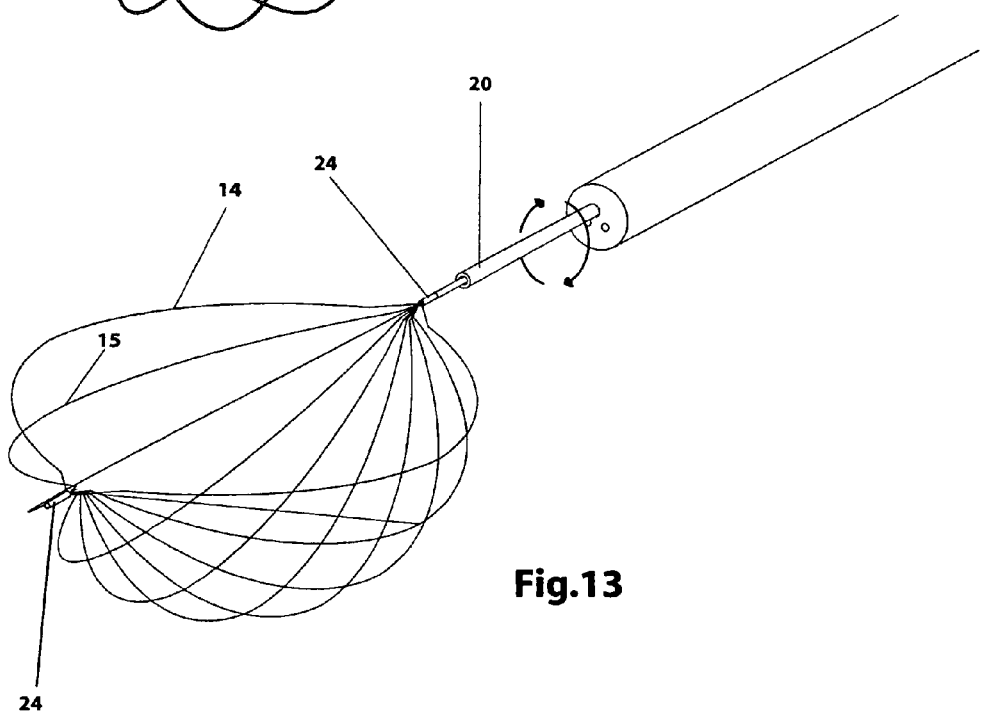
FIG. 13 depicts the catch basket in the oval configuration adapted for parallel use with a separate cauterizing snare.
Figure 17:
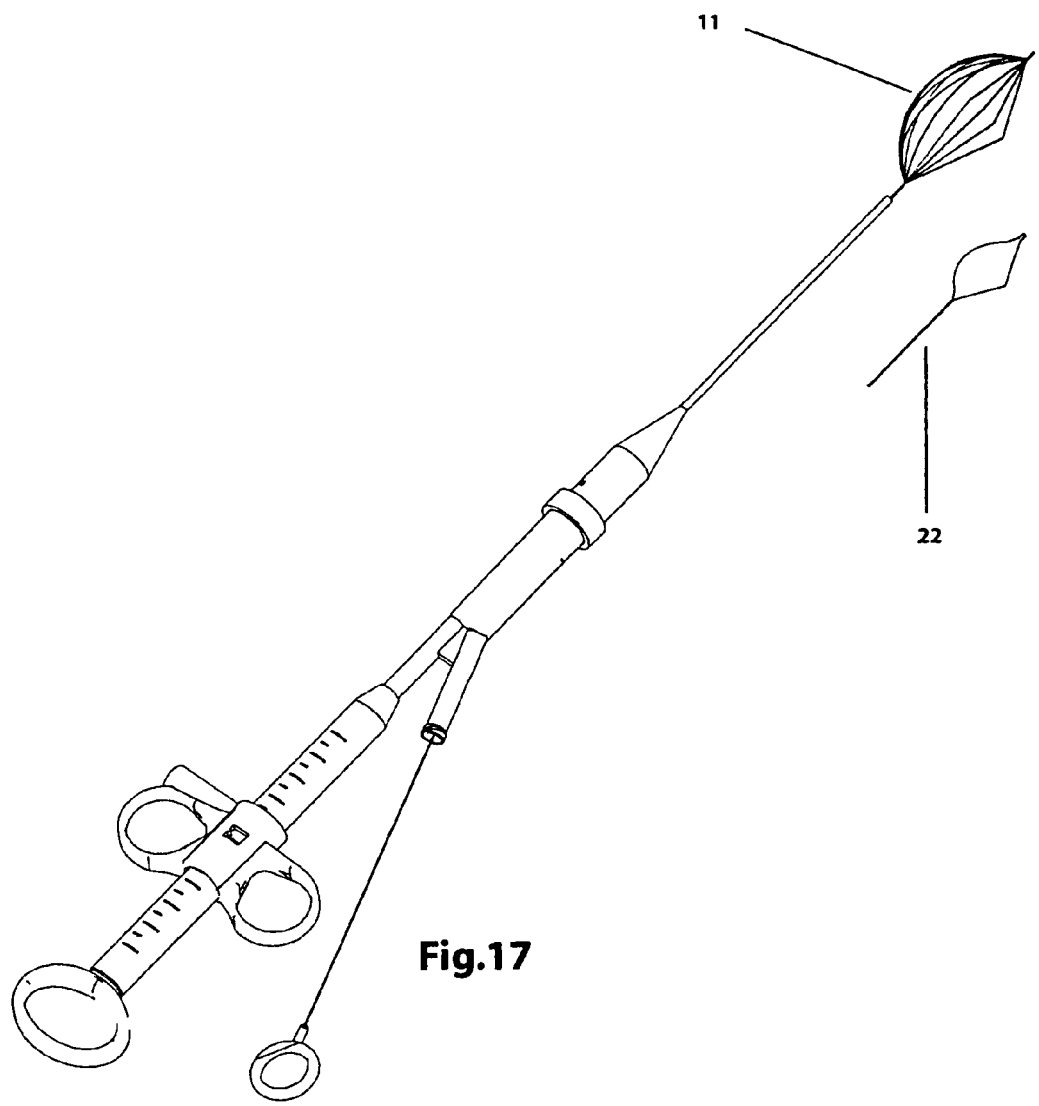
FIG. 17 depicts the parallel deployment of the device of FIG. 15 with a separately operated snare.
Figure 18:
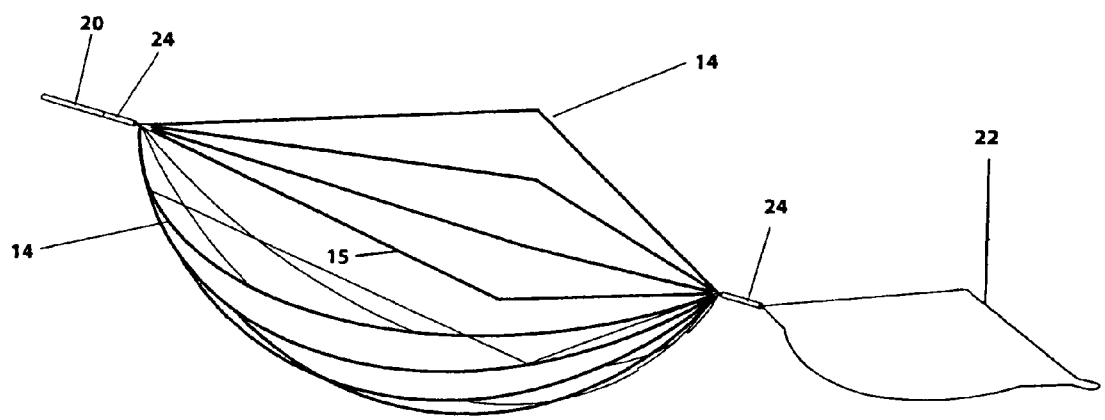
FIG. 18 is an enlarged view of the device of FIG. 16 showing the snare at the distal end of the crescent shaped basket.
Figure 24:
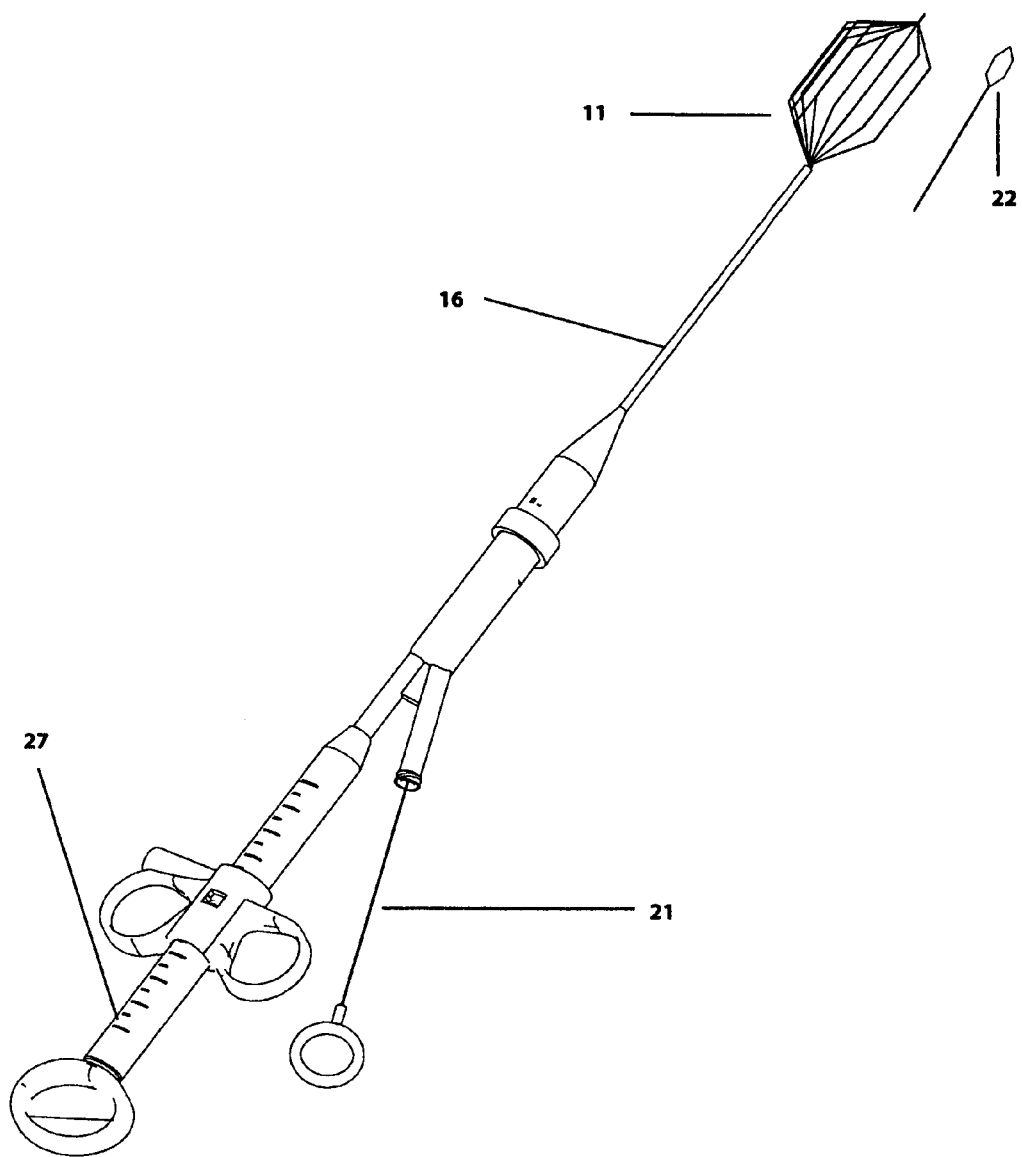
FIG. 24 depicts a deployment of the device of FIG. 20 in concert with an independently controlled snare.

FIGS. 11, 17, and 24, depict modes of the device 10 which employs a double lumen catheter having two internal conduits with two control wires allowing the catch basket 11 and the snare 22 to be independently manipulated inside the body of the patient. The lumen 20 engaging the catch basket 11 at a distal end provides means to translate and rotate the catch basket 11 inside the body of the patient. A second control wire or lumen 21 has the snare 22 engaged at a distal end. Both the first lumen 20 and second lumen 21 are translateable into and out of the distal end of the catheter 16 independently, thereby allowing the surgeon more options during a procedure.

Figure 14:
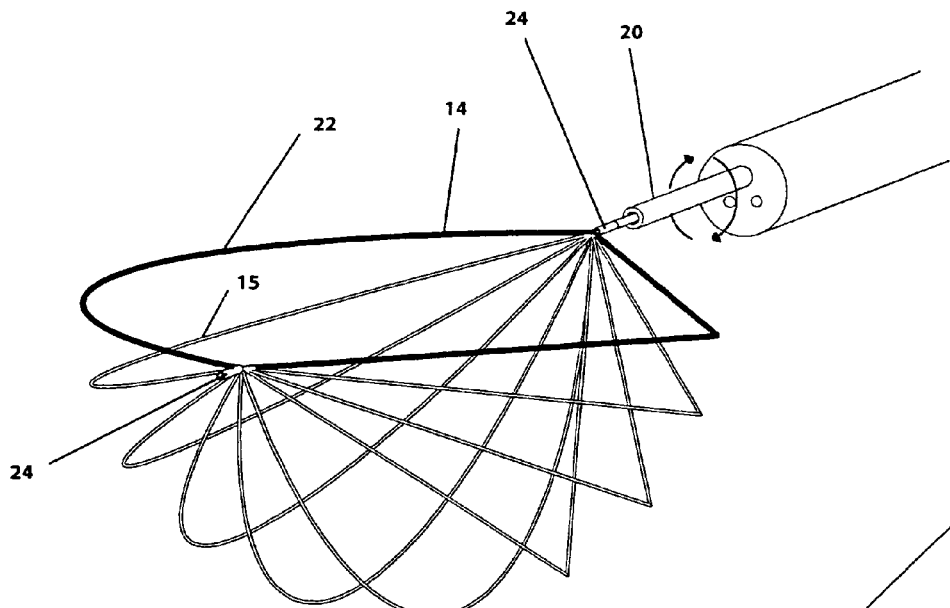
FIG. 14 shows an embodiment of the device having a crescent configuration defined by the similarly formed wires and with the cauterization snare being integral to the mouth as in FIG. 12.
Figure 15:
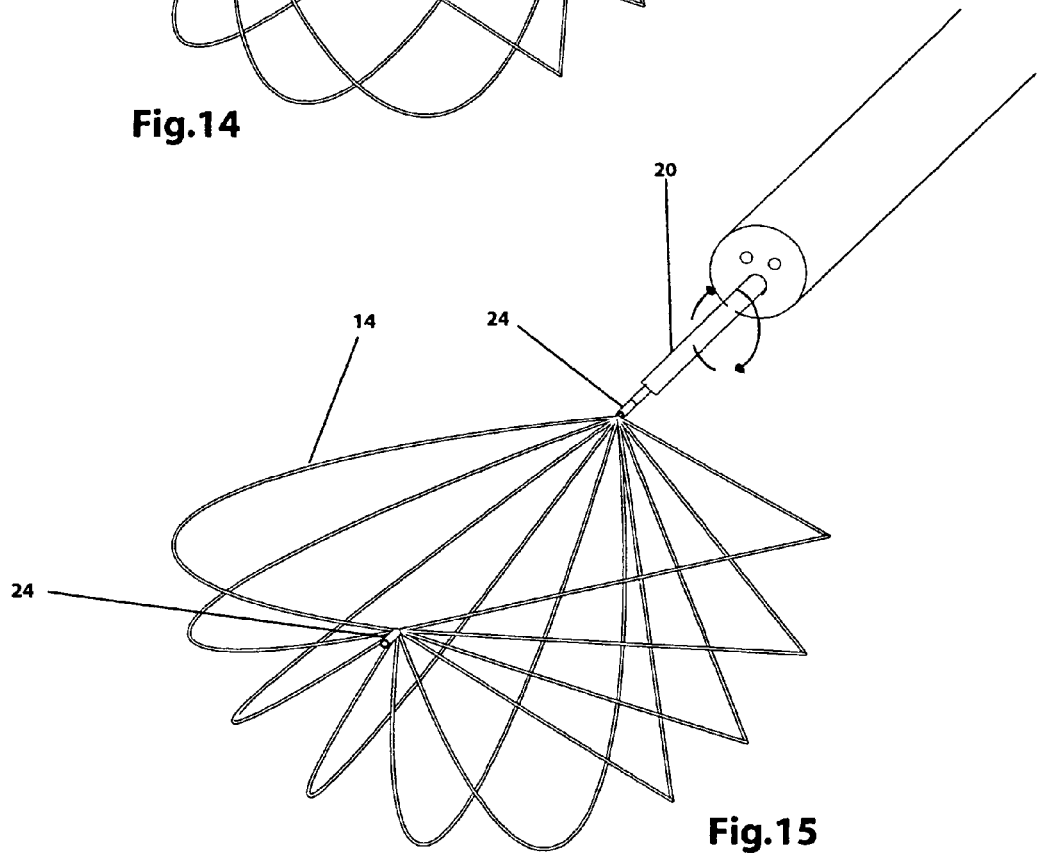
FIG. 15 depicts the crescent embodiment of the device adapted for use with a separate snare device.
Figure 16:
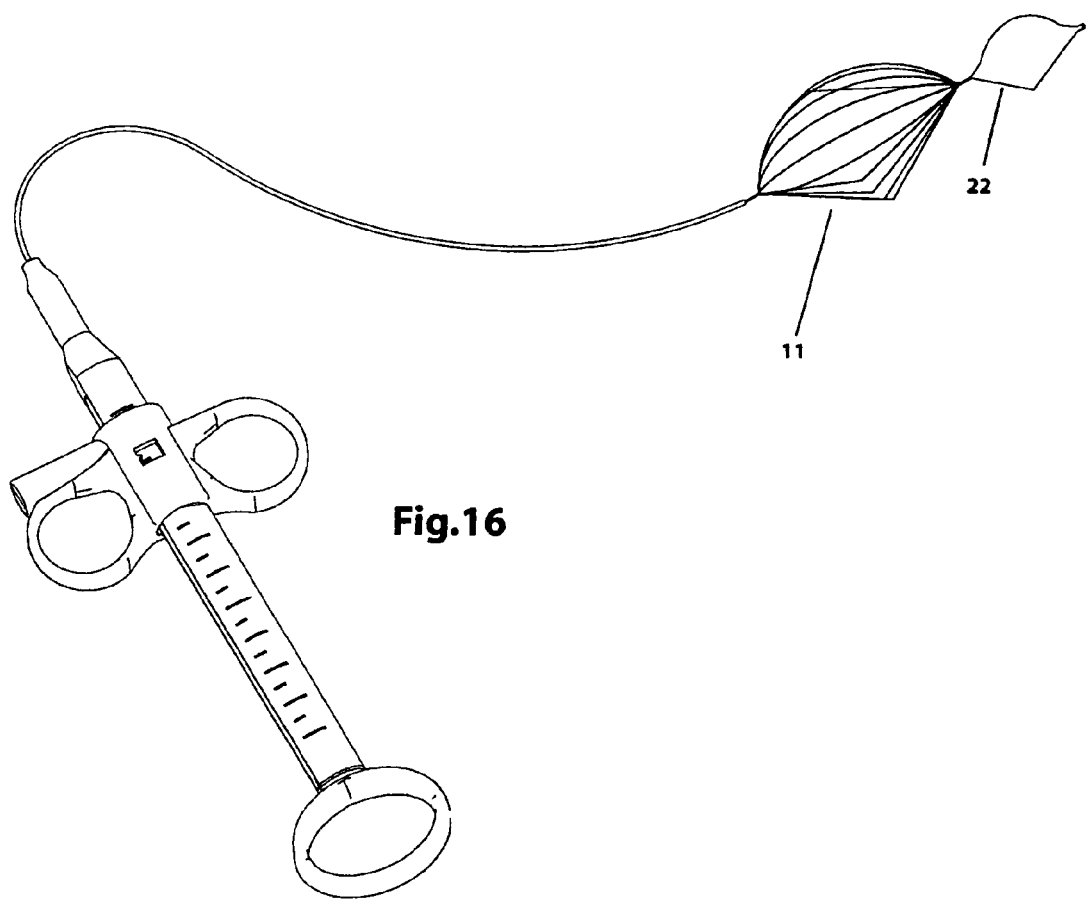
FIG. 16 shows an embodiment of the crescent shaped mode of the device with the snare extending from the distal end of the formed catch basket similar to that of the oval mode in FIG. 2.
Figure 19:
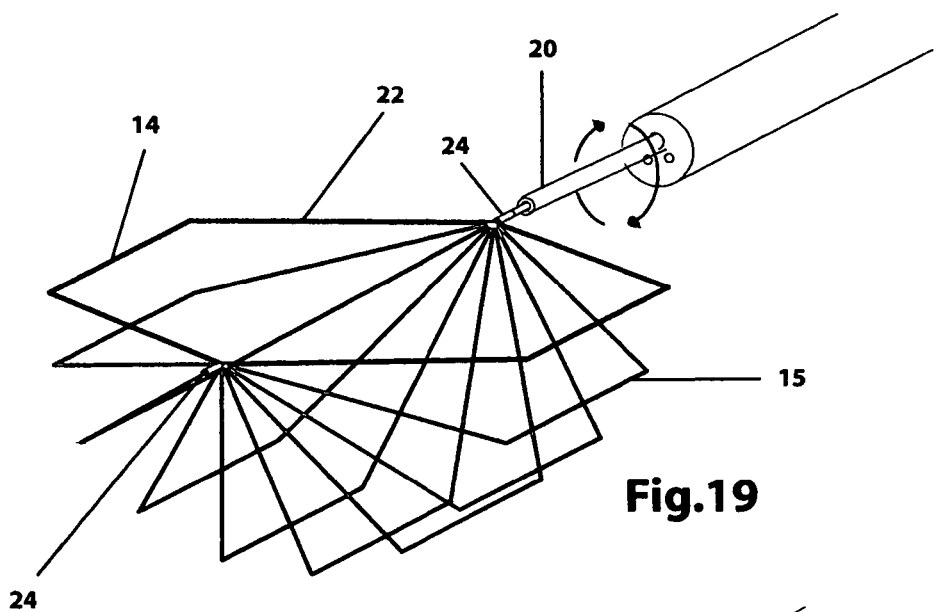
FIG. 19 depicts a hexagonal shape of the catch basket formed by the radially oriented wires and a mouth portion that concurrently functions as the cauterizing snare component.
Figure 20:
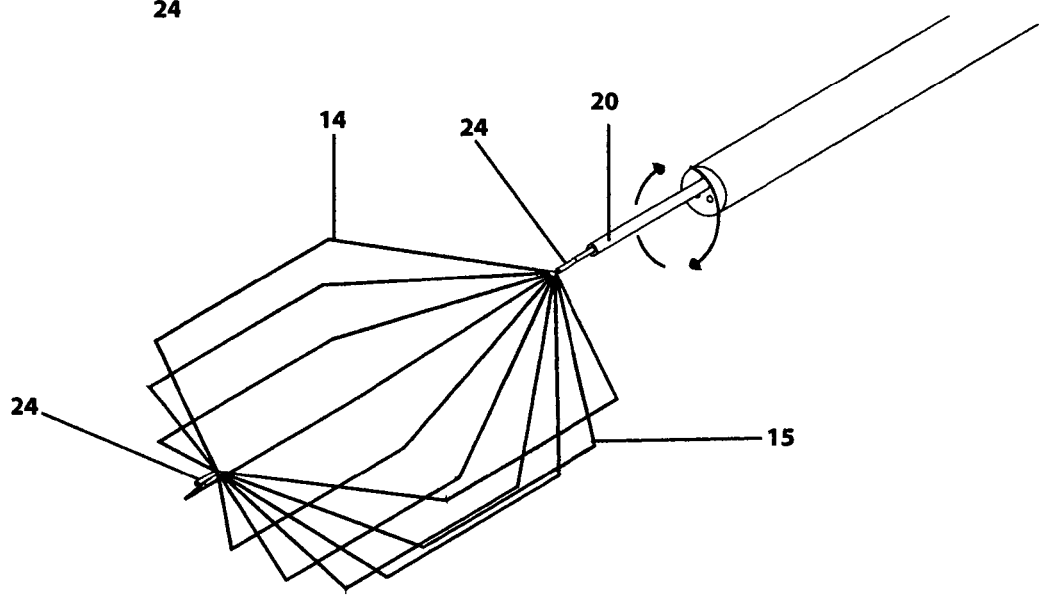
FIG. 20 shows a hexagonal shaped mode of the device adapted for separate and parallel deployment with a snare.
Figure 21:
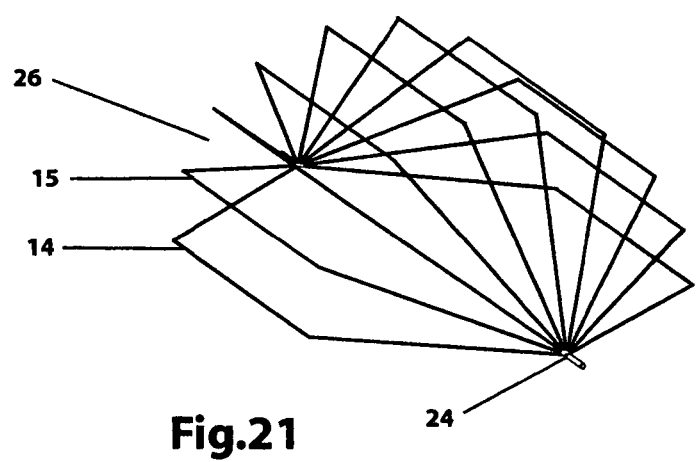
FIG. 21 depicts a rear perspective view of the hexagonal shaped device defined by the shapes of the individually radially oriented wires.
Figure 22:
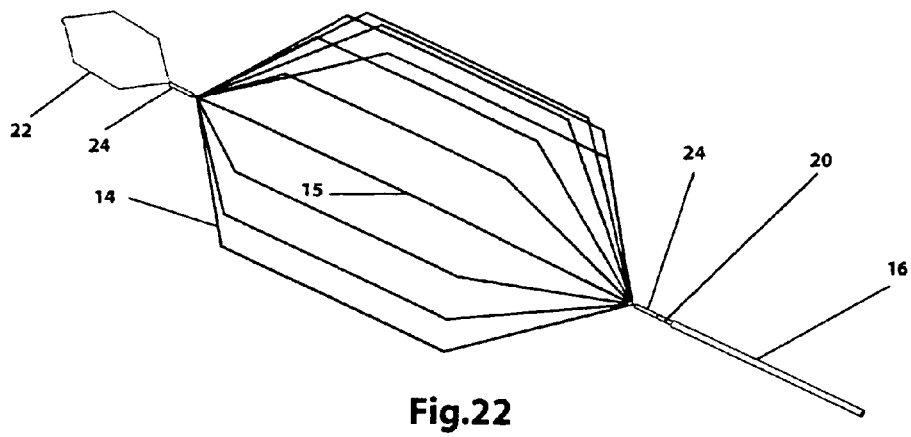
FIG. 22 depicts a hexagonal shaped mode of the device with a hexagonal snare engaged at the distal end of the formed catch basket.
Figure 23:
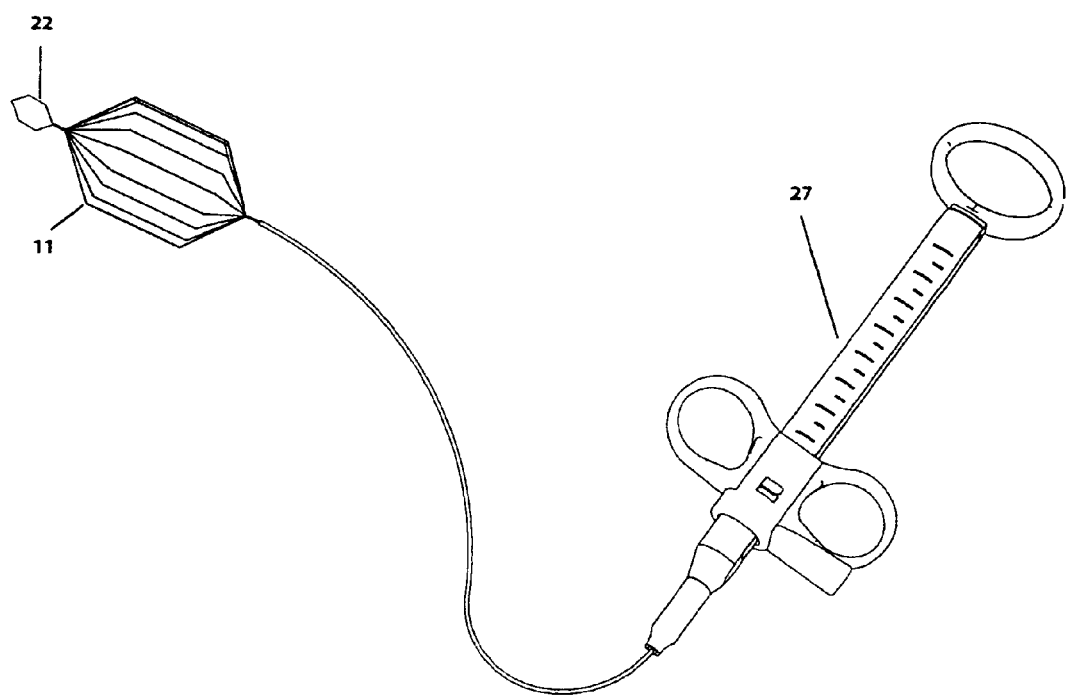
FIG. 23 shows a deployment of the device of FIG. 22.

As noted above, FIG. 12 shows an oval embodiment of the device 10 which is especially preferred having the cauterization snare 22 formed by the first wires 14 in the oval shape. FIG. 14 depicts a similar configuration in a crescent shape, and FIG. 19 depicts the integral mode of the device in a hexagonal shape. Of course other shapes may be employed, but the depicted shapes achieve an especially large aperture 12 when the opposing first wires 14 are fixed in position in a plane and also allow the aperture 12 to collapse to small sizes and naturally enlarge as the space allows.

By placing the snare 22 integral to the catch basket 11 using the first wires 14 to form it, the catch basket 11 may be positioned to surround the tissue 30 as it is removed, thus saving a time-consuming step for the surgeon. Formation would be accomplished by using non-conducting material, or insulated wires for the second wires 15, and a non-insulated first wire 14. The device in this mode would thus be positioned to catch the removed tissue 30 and the first wires 14 energized to remove it.

The method and components shown in the drawings and described in detail herein disclose arrangements of elements of particular construction, and configuration for illustrating preferred embodiments of structure of the present compressor invention. It is to be understood, however, that elements of different construction and configuration, and using different steps and process procedures, and other arrangements thereof, other than those illustrated and described, may be employed for providing a surgical retrieval device and method in accordance with the spirit of this invention.

As such, while the present invention has been described herein with reference to particular embodiments thereof, a latitude of modifications, various changes and substitutions are intended in the foregoing disclosure, and will be appreciated that in some instance some features of the invention could be employed without a corresponding use of other features, without departing from the scope of the invention as set forth in the following claims. All such changes, alternations and modifications as would occur to those skilled in the art are considered to be within the scope of this invention as broadly defined in the appended claims.

Further, the purpose of the foregoing abstract of the invention, is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting, as to the scope of the invention in any way.

What is claimed is:

1. A surgical retrieval apparatus comprising:
   a plurality of radially oriented shaped members extending substantially equidistantly spaced around an axis;
   each of said shaped members extending from a first end to a respective second end, and each having a shape;

means to maintain said plurality of shaped members in a fixed engagement around said axis;

said shape of said members in said fixed engagement, defining a catch basket said catch basket having a basket shape;

a plurality of gaps formed in between said plurality of radially oriented shaped members;

a mouth to said catch basket defined by an aperture formed of a first pair of said shaped members in said fixed engagement and opposite each other, both of said first pair substantially located in the same first plane;

said shape of said first pair of said shaped members thereby defining a mouth shape and a mouth area;

a first end of said catch basket at an intersection of all said first ends of said shaped members, in an engagement to a distal end of a single control wire translatably engaged within a single conduit;

said catch basket collapsible to a collapsed position having said intersection and at least a portion of said catch basket located inside said conduit, when said distal end of said control wire translates within said conduit;

said catch basket deployable to a deployed position when said intersection, engaged to said distal end of said control wire, translates outside of said conduit; and said catch basket assuming said basket shape, when in said deployed position, whereby said gaps provide substantially unimpeded viewing for a camera therethrough wherein communicated images from said camera can be employed to guide said catch basket to capture a target component through said mouth and into said catch basket whereupon said catch basket can be moved to said collapsed position to capture said target component for removal.

2. The device of claim 1 wherein said plurality of shaped members are wires formed of shape-memory material whereby said catch basket is translateable between said collapsed position and said deployed position repeatedly and maintains said catch basket shape and said mouth shape.

3. The device of claim 1 additionally comprising:
said first pair of said shaped members being electrically conductible and in electrical communication with each other;
said first pair of shaped members in said communication thereby defining a cauterizing snare;
means for electrical insulation of a remaining of said plurality of shaped members from electrical communication with either of said first pair; and
means to communicate electric power to said cauterizing snare for user determined periods of time.

4. The device of claim 2 additionally comprising:
said first pair of said shaped members being electrically conductible and in electrical communication with each other;
said first pair of shaped members in said communication thereby defining a cauterizing snare;
means for electrical insulation of a remaining of said plurality of shaped members from electrical communication with either of said first pair; and
means to communicate electric power to said cauterizing snare for user determined periods of time.

5. The device of claim 1 additionally comprising:
a snare engaged at a second end of said catch basket opposite said first end;
said snare formed by two opposing shaped side members defining a snare aperture therebetween and a snare aperture shape;
said snare shaped side members positioned to occupy said first plane;
said snare projecting away from said first end of said catch basket in a projecting position; and
means to communicate electric power to said first pair of said shaped members for user determined periods of time.

6. The device of claim 2 additionally comprising:
a snare engaged at a second end of said catch basket opposite said first end;
said snare formed by two opposing shaped side members defining a snare aperture therebetween and a snare aperture shape;
said snare shaped side members positioned to occupy said first plane;
said snare projecting away from said first end of said catch basket in a projecting position; and
means to communicate electric power to said first pair of said shaped members for user determined periods of time.

7. The device of claim 5 additionally comprising:
said snare side members formed of shape-memory material wherein said catch snare is translateable between a compressed position and said projecting position repeatedly, and maintains said snare aperture shape during repeated translations from said compressed position back to said projecting position.

8. The device of claim 6 additionally comprising:
said snare side members formed of shape-memory material wherein said catch snare is translateable between a compressed position and said projecting position repeatedly, and maintains said snare aperture shape during repeated translations from said compressed position back to said projecting position.

9. The device of claim 1 additionally comprising:
said mouth shape being one of a group of shapes including an oval, a crescent, and a hexagon.

10. The device of claim 2 additionally comprising:
said mouth shape being one of a group of shapes including an oval, a crescent, and a hexagon.

11. The device of claim 3 additionally comprising:
said mouth shape being one of a group of shapes including an oval, a crescent, and a hexagon.

12. The device of claim 4 additionally comprising:
said mouth shape being one of a group of shapes including an oval, a crescent, and a hexagon.

13. The device of claim 5 additionally comprising:
said mouth shape being one of a group of shapes including an oval, a crescent, and a hexagon.

14. The device of claim 6 additionally comprising:
said mouth shape being one of a group of shapes including an oval, a crescent, and a hexagon.

15. The device of claim 7 additionally comprising:
said snare aperture shape being one of a group of shapes including an oval, a crescent, and a hexagon.

16. The device of claim 8 additionally comprising:
said snare aperture shape being one of a group of shapes including an oval, a crescent, and a hexagon.

17. The device of claim 15 adapted for employment in combination with any of a gastroscope, colonoscope, sigmoidoscope, bronchoscope, laparoscope, Esophagoscope, and Nasolaryngoscope, to retrieve organic or inorganic matter from an animal or human.

18. The device of claim 1 additionally comprising:
means to selectably rotate said control wire in said conduit providing means to remotely rotate said catch basket.

19. The device of claim 4 additionally comprising:
means to selectably rotate said control wire in said conduit providing means to remotely rotate said catch basket, and said cauterizing snare.

20. The device of claim 8 additionally comprising:
means to selectably rotate said control wire in said conduit providing means to remotely rotate said catch basket and said snare.

21. A surgical catheterization and retrieval apparatus used in combination with any optical or imaging device to remove protrusions from an anatomical duct or passage comprising:
one or more pre-shaped members each having a first end and a distal end;
each of said pre-shaped members having a shape;
said shape including but not limited to circular, oval, crescent, polygon or any combination of straight, angled or curved segments;
said pre-shaped members arranged in a radial configuration to form a catch basket shape;
a loop formed of one or more additional pre-shaped members each having a first end and a distal end;
each of said additional pre-shaped members having a shape;
said shape of said additional pre-shaped members including but not limited to circular, oval, crescent, polygon or any combination of straight, angled or curved segments;
said loop forming an electrical conductive path thereby forming a cauterizing snare;
means to communicate power to said cauterizing snare;
said distal end of said pre-shaped members forming said cauterizing loop being arranged in proximity with said distal end of said pre-shaped members forming said catch basket;
said first ends of said pre-shaped members forming cauterizing snare and said first ends of said pre-shaped members forming said catch basket all being in an engagement to an engagement point at a distal end of a single control wire translatably engaged through a conduit; and
wherein said control wire is adapted to move said engagement and said first ends of both said cauterization snare and said catch basket, to a position within said conduit where an area of said mouth is reduced in concert with said power being communicated to said cauterization snare, whereby material extending into said mouth may be cauterized and a severed portion of said material may be simultaneously caught by said catch basket.

22. A surgical catheterization and retrieval apparatus of claim 21 further comprising:
each of said pre-shaped members defines a plane that passes through said first end and said distal end of said pre-shaped member and at least one other point along said shape of said pre-shaped member; and
said one or more pre-shaped members arranged so that said planes formed by said one or more pre-shaped members intersect essentially in a line extending between said first ends and said distal ends of said one or more pre-shaped members.

23. A surgical catheterization and retrieval apparatus of claim 21 further comprising:
said pre-shaped members forming said catch basket having electrical insulation thereon.

24. A surgical catheterization and retrieval apparatus of claim 23 further comprising:
each of said pre-shaped members defines a plane that passes through said first end and said distal end of said pre-shaped member and at least one other point along said shape of said pre-shaped member; and
said one or more pre-shaped members arranged so that said planes formed by said one or more pre-shaped members intersect essentially in a line extending between said first ends and said distal ends of said one or more pre-shaped members.

25. A surgical catheterization and retrieval apparatus of claim 21 further comprising:
a first end of said cauterizing snare and said first ends of said pre-shaped members of said catch basket being in said engagement to the distal end of a said control wire providing for a common rotation about said axis of said control wire when said control wire is rotated.

26. A surgical catheterization and retrieval apparatus of claim 25 further comprising:
each of said pre-shaped members defines a plane that passes through said first end and said distal end of said pre-shaped member and at least one other point along said shape of said pre-shaped member; and
said one or more pre-shaped members arranged so that said planes formed by said one or more pre-shaped members intersect essentially in a line extending between said first ends and said distal ends of said one or more pre-shaped members.

27. A surgical catheterization and retrieval apparatus of claim 21 further comprising:
means for connecting two or more of said pre-shaped members in fixed relation.

28. A surgical catheterization and retrieval apparatus of claim 27 further comprising:
each of said pre-shaped members defines a plane that passes through said first end and said distal end of said pre-shaped member and at least one other point along said shape of said pre-shaped member; and
said one or more pre-shaped members arranged so that said planes formed by said one or more pre-shaped members intersect essentially in a line extending between said first ends and said distal ends of said one or more pre-shaped members.

29. A surgical catheterization and retrieval apparatus of claim 21 further comprising:
an angle formed by the planes of the one or more pre-shaped members measured in a plane orthogonal to said line where the planes of said one or more pre-shaped members essentially intersect;
said angle measured from a first plane of a first of one or more formed members to a last plane of a last one or more formed members and passing through any intervening planes; and
said angle being less than 180 degrees.

30. A surgical catheterization and retrieval apparatus of claim 29 further comprising:
each of said pre-shaped members defines a plane that passes through said first end and said distal end of said pre-shaped member and at least one other point along said shape of said pre-shaped member; and
said one or more pre-shaped members arranged so that said planes formed by said one or more pre-shaped members intersect essentially in a line extending between said first ends and said distal ends of said one or more pre-shaped members.

31. A surgical catheterization and retrieval apparatus of claim 21 further comprising:
said pre-shaped members made from shape memory materials.

32. A surgical catheterization and retrieval apparatus of claim 31 further comprising:
   each of said pre-shaped members defines a plane that passes through said first end and said distal end of said pre-shaped member and at least one other point along said shape of said pre-shaped member; and
   said one or more pre-shaped members arranged so that said planes formed by said one or more pre-shaped members intersect essentially in a line extending between said first ends and said distal ends of said one or more pre-shaped members.

33. A surgical catheterization and retrieval apparatus of claim 21 further comprising:
   said optical and imaging devices including but not limited to a gastroscope, colonoscope, sigmoidoscope, bronchoscope, laparoscope, esophagoscope, Nasolaryngoscope, floroscope, MRI or CAT scan.

* * * * *